United States Patent
Ortac et al.

(10) Patent No.: US 9,909,172 B2
(45) Date of Patent: Mar. 6, 2018

(54) NON-THERMAL CYCLING FOR POLYMERASE CHAIN REACTION

(71) Applicant: The Regents of the University of California, Oakland, CA (US)

(72) Inventors: Inanc Ortac, La Jolla, CA (US); Sadik C. Esener, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 23 days.

(21) Appl. No.: 15/224,873

(22) Filed: Aug. 1, 2016

(65) Prior Publication Data

US 2016/0340716 A1    Nov. 24, 2016

Related U.S. Application Data (62) Division of application No. 13/923,337, filed on Jun. 20, 2013, now Pat. No. 9,410,171.

(60) Provisional application No. 61/662,301, filed on Jun. 20, 2012.

(51) Int. Cl.
| | | |
|---|---|---|
| C12Q 1/68 | (2006.01) | |
| C12P 19/34 | (2006.01) | |
| B01L 3/00 | (2006.01) | |

(52) U.S. Cl.
CPC .......... *C12Q 1/686* (2013.01); *B01L 3/50273* (2013.01); *C12P 19/34* (2013.01); *B01L 2200/0694* (2013.01); *B01L 2300/0816* (2013.01); *B01L 2300/0883* (2013.01); *B01L 2400/0421* (2013.01)

(58) Field of Classification Search
None
See application file for complete search history.

(56) References Cited

U.S. PATENT DOCUMENTS

| | | |
|---|---|---|
| 6,395,489 B1 | 5/2002 | Stanley |
| 6,908,770 B1 | 6/2005 | McDevitt et al. |
| 7,172,864 B1 | 2/2007 | Heller et al. |
| 2008/0166770 A1 | 7/2008 | Morita et al. |
| 2012/0028342 A1* | 2/2012 | Ismagilov .......... B01L 3/502738 435/283.1 |
| 2012/0322076 A1 | 12/2012 | Chang et al. |

OTHER PUBLICATIONS

Florescu, Ana Maria, "Modeling of DNA and DNA-Protein Interactions", Diss. University of Grenoble, France, 2010, 191 pages.

Radtkey et al., "Rapid, high fidelity analysis of simple sequence repeats on an electronically active DNA microchip" Nucleic Acids Research, 2000, vol. 28, No. 7, 6 pages.

Heller, Michael J. "DNA microarray technology: devices, systems, and applications." Annual review of biomedical engineering 4.1 (2002): pp. 129-153.

Sosnowski et al., "Rapid determination of single base mismatch mutations in DNA hybrids by direct electric field control", Proc. Natl. Acad. Sci. USA, 1997 vol. 94, pp. 1119-1123.

Zhang, Chunsun et al., "Miniaturized PCR chips for nucleic acid amplification and analysis: latest advances and future trends", Nucleic Acids Research, 2007, pp. 1-15.

\* cited by examiner

*Primary Examiner* — David C Thomas
(74) *Attorney, Agent, or Firm* — Perkins Coie LLP (57) ABSTRACT

Techniques, systems, and devices are disclosed for non-thermal cycling of polymerase chain reaction (PCR). In one aspect, a method for cycling PCR includes receiving an electrolytic fluid including ions, primers, polymerase enzymes, nucleotides, and a double-stranded nucleic acid in a fluid chamber having a first electrode and a second electrode, applying an electric field across the first and the second electrodes to generate a first pH level of the electrolytic fluid to denature the double-stranded nucleic acid to at least partial single strands, and applying a second electric field across the first and second electrodes to produce a second pH level of the electrolytic fluid, in which the second pH level enables binding of a polymerase enzyme and a primer with a corresponding segment of the single strands.

4 Claims, 10 Drawing Sheets

NON-THERMAL CYCLING FOR POLYMERASE CHAIN REACTION

CROSS REFERENCE TO RELATED APPLICATIONS

This patent document is a division of U.S. application Ser. No. 13/923,337, filed Jun. 20, 2013, entitled "NON-THERMAL CYCLING FOR POLYMERASE CHAIN REACTION," which claims the benefit of priority of U.S. Provisional Patent Application No. 61/662,301, entitled "NON-THERMAL CYCLING FOR POLYMERASE CHAIN REACTION," filed on Jun. 20, 2012. The entire content of the aforementioned patent application is incorporated by reference as part of the disclosure of this patent document.

TECHNICAL FIELD

This patent document relates to polymerase chain reaction (PCR) technologies.

BACKGROUND

Deoxyribonucleic acid (DNA) is a molecule that encodes the genetic information of living organisms. A naturally-occurring double-stranded DNA includes a linked chain of alternating deoxyribose sugars and phosphate groups as a backbone for four nucleotide bases, e.g., including adenine (A), cytosine (C), guanine (G), thymine (T), which are attached to the deoxyribose sugar. The genetic information of DNA is encoded as a sequence of these nucleotide bases. The four nitrogen bases can form hydrogen bonds that hold two individual strands of the DNA together. For example, in naturally-occurring double-stranded DNA, adenine bonds to thymine (A=T) and cytosine bonds to guanine (C≡G). The A=T and C≡G bonds are two different types of hydrogen bonds formed by the base pairs. Adenine forms two hydrogen bonds with thymine (A=T) and cytosine forms three hydrogen bonds with guanine (C≡G). For example, the energy of formation of N—H . . . O bonds is approximately 8 kJ/mol, and the energy of formation of N—H . . . N bonds is approximately 13 kJ/mol (e.g., where the dotted line represents the hydrogen bond).

Polymerase chain reaction (PCR) is a widely used method for in vitro DNA amplification. PCR is commonly used in molecular biology to make copies of a particular region of DNA starting from a few copies up to several orders of magnitude. It involves a series of cycles involving different temperature points to facilitate DNA melting and enzymatic replication. However, using thermocycling to facilitate DNA melting and enzymatic replication (e.g., switching between double- and single-stranded DNA) is not necessarily desirable. Heating and cooling can limit device design, and thermocycling can be a power-hungry process.

SUMMARY

Techniques, systems, and devices are disclosed for implementing PCR using charge or pH cycling. Electrodes can be placed on different sides of an electrolytic fluid including ions, primers, polymerase enzymes, nucleotides and one or more nucleic acids in the PCR processing to create a spatial distribution of charges in the electrolytic fluid between the electrodes to control the spatial distribution of the pH level inside the electrolytic fluid between the electrodes. The electrical field applied to the electrodes is controlled to change the pH levels to cause cycling of the PCR reactions for amplifying a nucleic acid template, e.g., DNA.

In one aspect of the disclosed technology, a method for cycling PCR includes receiving an electrolytic fluid including ions, primers, polymerase enzymes, nucleotides, and a double-stranded nucleic acid in a fluid chamber having a first electrode and a second electrode, applying an electric field across the first and the second electrodes to generate a first pH level of the electrolytic fluid to denature the double-stranded nucleic acid to at least partial single strands, and applying a second electric field across the first and second electrodes to produce a second pH level of the electrolytic fluid, in which the second pH level enables binding of a polymerase enzyme and a primer with a corresponding segment of the single strands. In some implementations of the method, for example, the second pH level can enable synthesis of new complementary nucleic acid strands using the at least partial single strands. In other implementations, for example, the method can further include applying a third electric field across the first and second electrodes to produce a third pH level of the electrolytic fluid, in which the third pH level enables synthesis of new complementary nucleic acid strands using the at least partial single strands.

In another aspect, a device for cycling PCR includes a container having an interior surface formed of an electrically insulative material and structured to contain an electrolytic fluid including ions, primers, polymerase enzymes, nucleotides, and a double-stranded nucleic acid, a first electrode and a second electrode configured on an interior surface of the container in contact with the electrolytic fluid, and a circuit electrically coupled to the first and second electrodes to apply a first electric field across the first and second electrode to generate a first pH level of the electrolytic fluid, in which the double-stranded nucleic acid is capable of denaturation to at least partial single strands at the first pH level, and to apply a second electric field across the first and second electrodes to generate a second pH level of the electrolytic fluid, in which the second pH level enables at least one of binding of a polymerase enzyme and a primer with a corresponding segment of the at least partial single strands or synthesis of new complementary nucleic acid strands from the nucleotides using the at least partial single strands.

In another aspect, a device for cycling PCR includes a substrate that is electrically insulating, a channel formed of an electrically insulative material on the substrate and structured to carry an electrolytic fluid including ions, primers, polymerase enzymes, nucleotides, and a double-stranded nucleic acid, a first electrode pair and a second electrode pair located in the channel in contact with the electrolytic surface and spaced apart along the channel, and a circuit electrically coupled to the first and second electrode pairs to apply a first electric field across the first electrode pair to generate a first pH level of the electrolytic fluid, in which the double-stranded nucleic acid is capable of denaturation to at least partial single strands at the first pH level, and to apply a second electric field across the second electrode pair to generate a second pH level of the electrolytic fluid, in which the second pH level enables at least one of binding of a polymerase enzyme and a primer with a corresponding segment of the at least partial single strands or synthesis of new complementary nucleic acid strands from the nucleotides using the at least partial single strands.

In another aspect, a portable PCR device on a chip includes a substrate that is electrically insulating, an enclosed channel formed of an electrically insulative material on the substrate and structured to carry an electrolytic fluid including ions, primers, polymerase enzymes, nucleotides, and a double-stranded nucleic acid, one or more ports to transfer the electrolytic fluid in or out of the channel, two or more electrode pairs located in the channel in contact with the electrolytic surface and spaced apart along the channel, and two or more electrical interface components electrically coupled to the corresponding two or more electrode pairs via electrically conductive conduits, in which the two or more electrode pairs are capable of receiving applied electrical signals from an external electrical circuit electrically coupled to the two or more electrical interface components, in which the applied electrical signals produce a first electric field across a first electrode pair to generate a first pH level of the electrolytic fluid such that the double-stranded nucleic acid is capable of denaturation to at least partial single strands at the first pH level, and produce a second electric field across a second electrode pair to generate a second pH level of the electrolytic fluid to enable at least one of binding of a polymerase enzyme and a primer with a corresponding segment of the at least partial single strands or synthesis of new complementary nucleic acid strands from the nucleotides using the at least partial single strands.

The subject matter described in this patent document can provide one or more of the following advantages and benefits. For example, the disclosed PCR cycling method can improve the cycling speed, reduce power consumption, and allow better reaction control, e.g., as compared to thermal cycling in conventional PCR. For example, the disclosed PCR methods, systems, and devices can be compatible with the existing sample preparation and detection schemes in current PCR techniques, e.g., offering a totally integrated approach that provides portability and increases overall reaction efficiency.

DETAILED DESCRIPTION

PCR processes based on thermal cycling can be implemented in various ways. One approach to achieving thermal cycling in PCR involves having the solution stationary and heating and cooling by an external source, and an alternative approach to thermal cycling involves creating constant temperature regions adjusted to different temperatures and continuously flowing the solution between these regions. Various thermal cycling techniques for PCR have certain practical limits and thus cannot address further needs for integrated, fast and portable systems.

Figure 1:
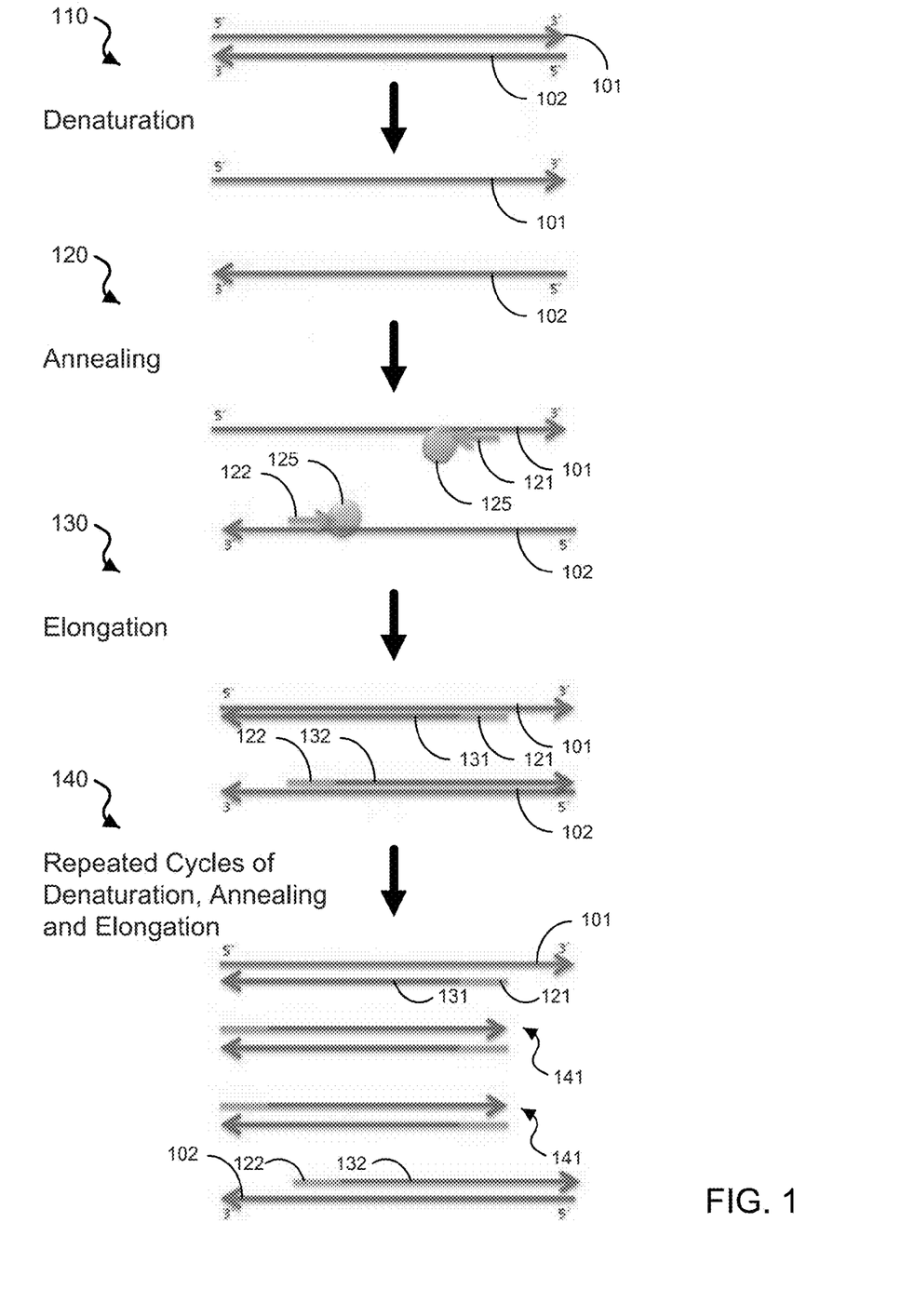
FIG. 1 shows an illustrative diagram of thermal cycling of PCR.

An example of a thermal-cycling-based PCR process is shown in FIG. 1. Three main stages are shown in this example in each thermal cycle: a denaturation stage 110, an annealing stage 120, and an elongation stage 130. A double-stranded DNA is shown in FIG. 1 to include a strand 101 and a strand 102 that run anti-parallel to each other. The 3' and 5' configurations refer to the direction the 3rd and 5th carbon on the deoxyribose sugar molecule is facing. The individual strands 101 and 102 are bonded together by hydrogen bonding to form the double-stranded DNA.

During the denaturation stage 110, the temperature is raised up to the melting (denaturation) point of the double-stranded DNA, e.g., to around 95° C., in order to disrupt the hydrogen bonds to yield single-stranded DNA molecules 101 and 102. Hydrogen bonds are much weaker than the covalent bonds in the rest of the molecule, so denaturation does not affect the primary structure of DNA and is a reversible process. In annealing step 120, the temperature is lowered (e.g., 55-68° C.) to anneal primers 121 and 122 to the single-stranded DNA templates 101 and 102, respectively. Primers are short DNA fragments with sequences complementary to a target region of a single-stranded template. During the annealing stage 120, polymerase enzymes 125 bind to the primer-template hybrid to start DNA synthesis. Later, the temperature is raised up to the optimum temperature of polymerase activity (e.g., 70-80° C. for TAQ polymerase) in the elongation stage 130. During the elongation stage 130, the polymerases 125 help synthesize new complementary strands 131 and 132 to the single-stranded templates 101 and 102 elongated from the primers 121 and 122, respectively, by attaching 5' phosphate group of the deoxynucleoside triphosphates (dNTP, building block of DNA) with the 3'-hydroxyl group at the end of the extending DNA strand. At the end of the thermal cycle, if there are no limiting substrates or reagents, the amount of DNA target is doubled. The thermal cycling process of denaturation 110, annealing 120, and elongation 130 can be repeated, as shown in the process 140, to produce copies of the DNA target, as shown as double-stranded DNA copies 141. For example, the temperature is raised back to the denaturation temperature again to start the next cycle. In each cycle, target DNA amount is doubled leading to exponential amplification of the specific DNA target. For example, a typical reaction can be around 30-40 cycles, and the duration of each cycle can comprise a few to several minutes, resulting in PCR processes needing hours to be implemented.

In various prior PCR processes, the temperature is controlled to modulate the binding dynamics of DNA, e.g., the switching between double-stranded and single-stranded DNA. However, the temperature is not the only parameter that can affect binding dynamics, although temperature is the most exploited parameter by others. Factors other than the temperature can also be used to affect the binding and initiate denaturation, including, e.g., the pH level, ion concentration, and certain denaturants such as urea or formamide. For example, at low pH, the nucleotide bases of DNA become protonated and repel the complementary base; and at high pH, the nucleotide bases lose protons and become negatively charged and also repel the complementary base. For example, for ion concentration, positive ions in the solution can shield the negatively charged phosphates in the backbone of the DNA; in low ion concentrations, the shielding can also be low increasing the repulsive forces and decreasing the melting temperature. For example, chemical agents like formamide or urea can destabilize hydrogen bonds by displacing hydrates or counter ions leading to similar effect of ion concentration.

Disclosed are methods, systems, and devices for amplifying nucleic acid sequences through non-thermal cycling PCR techniques including charge cycling or pH cycling. The disclosed non-thermal cycling PCR techniques may be used without thermal cycling in some implementations or in combination with thermal cycling in other implementations.

In one aspect, a method for cycling PCR includes receiving an electrolytic fluid including ions, primers, polymerase enzymes, nucleotides, and a double-stranded nucleic acid in a fluid chamber having a first electrode and a second electrode, applying an electric field across the first and the second electrodes to generate a first pH level of the electrolytic fluid to denature the double-stranded nucleic acid to at least partial single strands, and applying a second electric field across the first and second electrodes to produce a second pH level of the electrolytic fluid, in which the second pH level enables binding of a polymerase enzyme and a primer with a corresponding segment of the single strands. In some implementations of the method, for example, the second pH level can enable synthesis of new complementary nucleic acid strands using the at least partial single strands. In other implementations, for example, the method can further include applying a third electric field across the first and second electrodes to produce a third pH level of the electrolytic fluid, in which the third pH level enables synthesis of new complementary nucleic acid strands using the at least partial single strands.

For example, the locations where positive ions dominate create low pH regions, and the locations where negative ions dominate create high pH regions, e.g., each of these low and high pH regions can initiate denaturation. The denaturation, annealing, and elongation stages of PCR can be implemented using the disclosed method by creating charge distributions, e.g., which involve electrically manipulating small ions to form charge layers in the chamber volume, thereby controlling pH. For example, the denaturation, annealing, and elongation stages of the disclosed PCR cycling method can be several orders of magnitude faster than changing the temperature of the solution. For example, the duration of thermal equilibration can be on the order of several minutes, which significantly makes the stages of thermal cycling PCR such as denaturation quite long. The disclosed non-thermal PCR techniques include changing ion distributions in solutions through electric fields that can be on the order of microseconds to other sub-second durations, e.g., depending on the conductivity, ion diffusion rates, charge of ions and voltage applied.

Figure 2A:
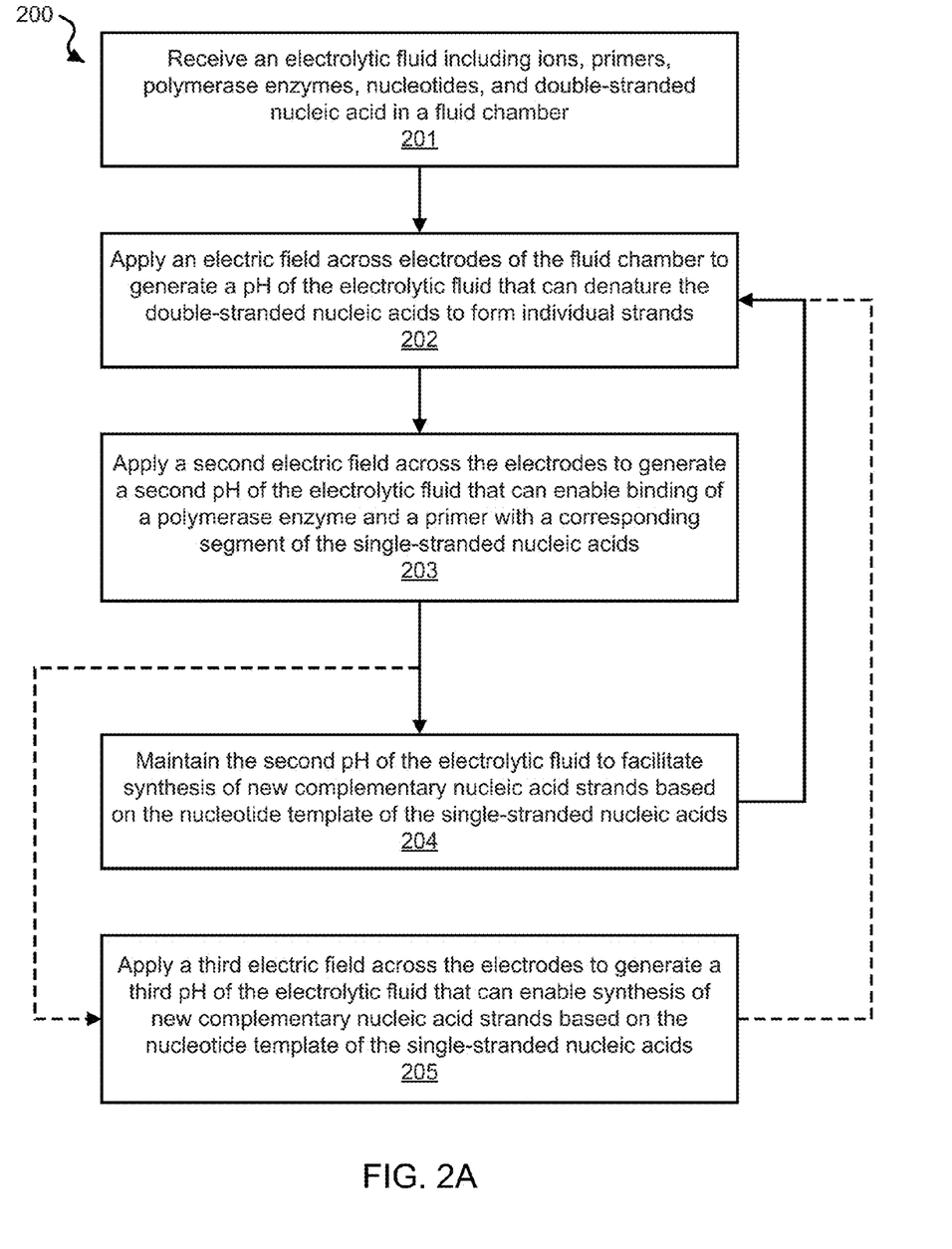
FIG. 2A shows a process diagram of an exemplary PCR cycling method of the disclosed technology.

FIG. 2A shows a process diagram of an exemplary PCR cycling method 200. The method 200 includes a process 201 to receive an electrolytic fluid in a fluid chamber. For example, the fluid chamber can be structured to include an interior surface formed of an electrically insulative material and having one or more electrodes. For example, the electrolytic fluid can include ions, e.g., including $H^+$, $OH^-$ and $Mg^{2+}$ among others, and PCR reagents, e.g., including primers, polymerase enzymes, nucleotides, and one or more double-stranded nucleic acid molecules. The method 200 includes a process 202 to apply an electric field across the electrodes of the fluid chamber containing the electrolytic fluid to generate a pH of the electrolytic fluid that denatures double-stranded nucleic acids, e.g., such as DNA, to single-stranded nucleic acids. For example, the degree of denaturation of the double-stranded nucleic acids can depend on the size of the double-stranded nucleic acids and the level of acidic or basic pH. In some instances, the process 202 can be controlled to form at least partial denaturation of the double-stranded nucleic acids, e.g., exposing one or more regions of the double-stranded nucleic acids as single-stranded segments. In some implementations, for example, the process 202 can include applying an electric charge on one electrode (e.g., positive or negative) while the other electrode remains neutral (substantially no net charge). For example, in some embodiments, the fluid chamber may include a single electrode. The method 200 includes a process 203 to apply a second electric field across the electrodes to generate a second pH level of the electrolytic fluid that can enable the binding of a polymerase enzyme and a primer with a corresponding complementary portion on one or both of the single-stranded nucleic acids. In some implementations, the method 200 includes a process 204 to substantially maintain the second pH level, e.g., by maintaining the second electric field across the electrodes, that can facilitate or allow synthesis of new complementary nucleic acid strands from the single-stranded nucleic acid templates. In other implementations, the method 200 includes a process 205 to apply a third electric field across the electrodes to generate a third pH level of the electrolytic fluid that can enable the synthesis of new complementary nucleic acid strands from the single-stranded nucleic acid templates. The PCR cycle can be repeated at process 202 as desired to amplify the nucleic acids, e.g., effectively doubling the amount of double-stranded nucleic acids per repetition of the PCR cycle.

In some implementations, for example, the fluid chamber can be configured to include a semi-permeable membrane that separates a first region from a second region, in which the first region includes the first electrode and the second region includes the second electrode. The semi-permeable membrane is permeable to ions and can allow the ions to traverse the membrane while being impermeable to large molecules including the primers, polymerase enzymes, nucleotides, and nucleic acids. The process 201 to receive the electrolytic fluid can include adding the primers, polymerase enzymes, nucleotides, and double-stranded nucleic acid into the first region or into the second region of the fluid chamber, thereby exposing the PCR reagents to either an acidic or a basic pH. In some implementations, the method can include a process to attach the polymerase enzymes to a surface of the fluid chamber, e.g., via covalent attachment to the electrodes or to an insulating layer, for example, on top of the electrodes. For example, polymerase enzymes can be attached to gold surfaces through thiol chemistry. In one example, the electrodes can be configured as gold electrodes, and functionalized self-assembled monolayers (e.g., alkanethiol molecules) can be attached to the gold electrodes by self-assembly and conjugated with polymerase, e.g., via carboxyl-amino conjugation chemistries. In another example, a layer of silicon dioxide can be grown on the surface of the electrodes, where enzymes can be attached with silane chemistry.

The applied electric fields create a spatial ion distribution in the electrolytic fluid including a first layer of first ions electrically attracted to an oppositely-charged electrode and a second layer of second ions electrically attracted to the first layer. The ion distribution depends on the dimensions and geometry of the electrodes, and applied voltage on electrodes (e.g., magnitude of the electric field), and ion concentrations in the electrolytic fluid. In some implementations, for example, the method 200 can include a process to select the magnitude and duration of the applied electric fields for each of the processes 202, 203, and 204 and/or 205. In some implementations, a DC electric field can be generated by applying a DC voltage across the electrodes. In other implementations, an ac electric field may be applied, e.g., which can also include a DC bias. For example, the spatial distribution of charge can be produced and controlled by manipulating the "double layer" in the electrolytic solution (e.g., PCR buffer solution) using the applied external electric fields, providing a field-controlled pH to essentially start and stop the reactions.

The "double layer" refers to two parallel layers, e.g., the first and second layers, surrounding the surface of an object when it is placed into a liquid. The first layer (Stern layer) includes a surface charge that is either positive or negative and is formed by ions adsorbed directly onto the object. The second layer (diffuse layer) is composed of ions attracted to the surface in order to electrically screen the first layer. The diffuse layer is made up of free ions loosely associated with the object. The double layer can extend up to micrometers depending on the ion concentration of the solution and charge on the surface. It is the region where the pH distribution is created.

Figure 2B:
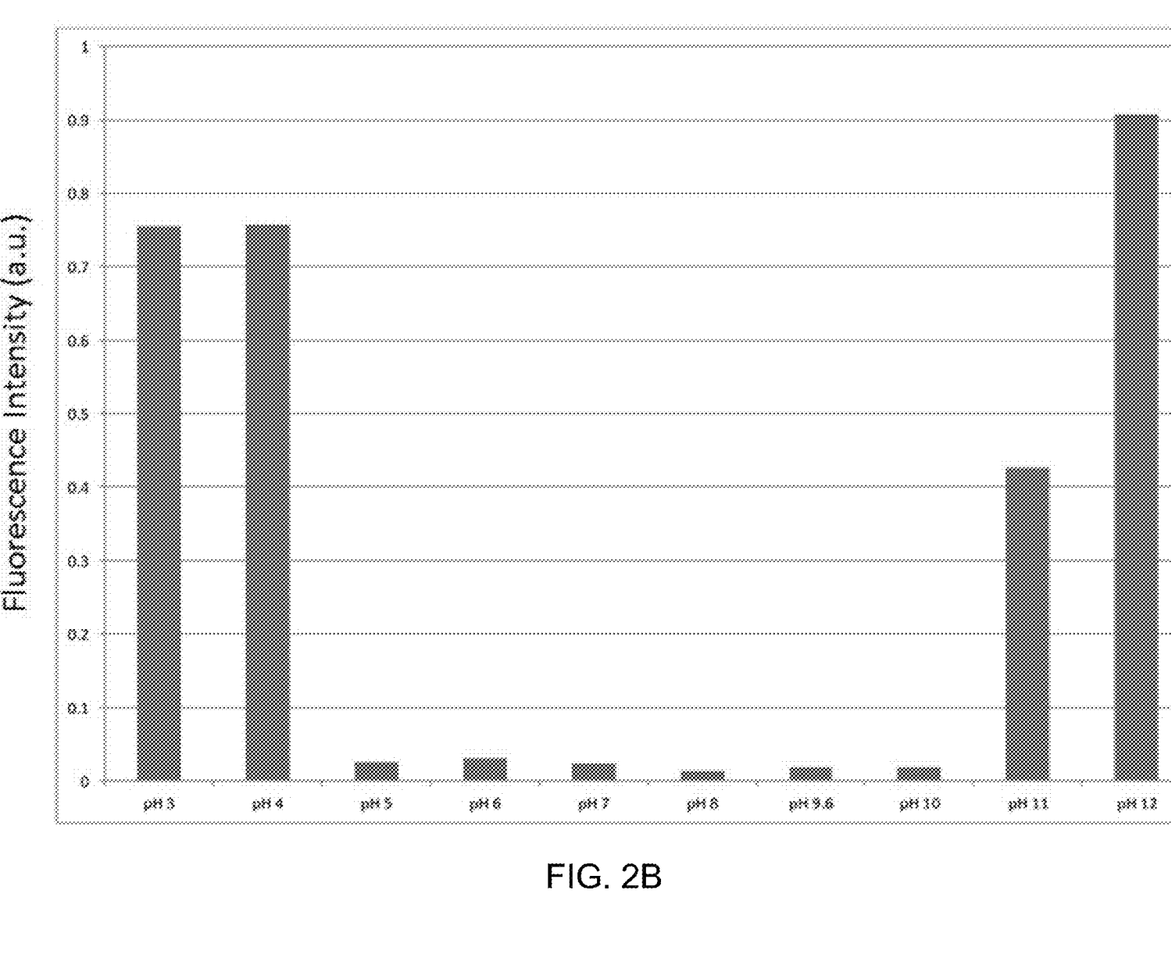
FIG. 2B shows a data plot depicting an exemplary pH distribution that can be produced during implementation of an exemplary method for pH cycling in PCR.

FIG. 2B shows a data plot depicting an exemplary pH distribution that can be produced during implementation of an exemplary method for pH cycling in PCR. For example, the data plot shows the fluorescence intensity during hybridization of two complementary nucleic acid strands (e.g., 20 nitrogen base pairs each), e.g., one with a fluorophore and the other with a quencher, at different pH levels in the exemplary fluidic chamber. As shown in the data plot, from pH 5 to pH 10, the two complementary strands are hybridized, therefore, fluorescence is quenched. However at acidic pH (e.g., pH 4 or less) and basic pH (e.g., pH 11 or greater), the complementary nucleic acid strands are separated from each other, thereby producing a fluorescence signal.

FIGS. 3A-3I show diagrams of exemplary spatial ion distributions produced by the applied electric charge at the electrodes of the fluid chamber.

Figure 3A:
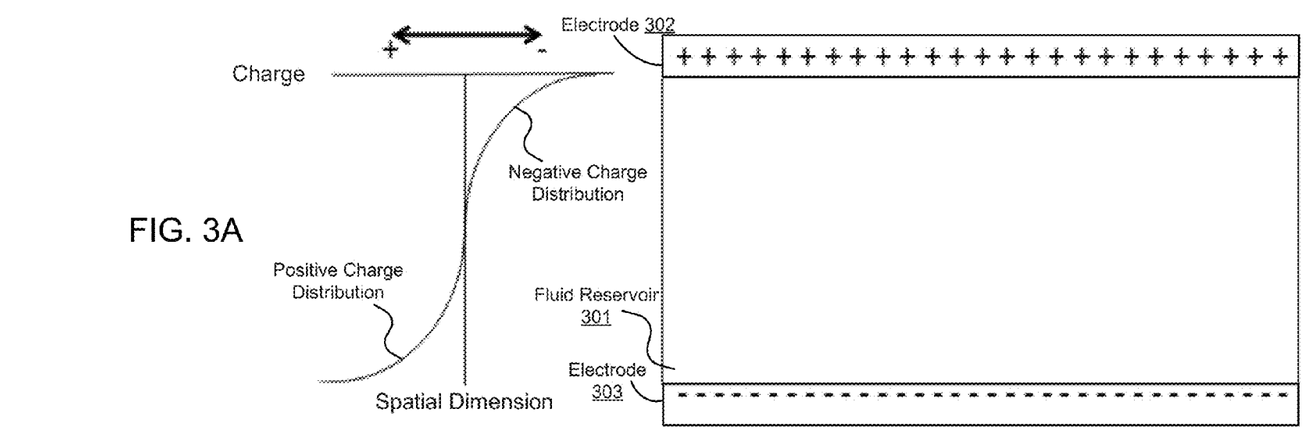
FIGS. 3A-3I show diagrams of exemplary spatial ion distributions produced by disclosed techniques using applied electric charge.

FIG. 3A shows a diagram depicting the charge distribution corresponding to a spatial dimension of a fluid reservoir 301, configured between two electrodes 302 and 303 in an exemplary non-thermal PCR device, in which a net positive charge is applied along the electrode 302 and a net negative charge is applied along the electrode 303, e.g., generating an electric field across the electrolytic fluid in the fluid reservoir. As shown in the diagram, a negative charge distribution (of negative ions of the electrolytic fluid) is at a maximum at the electrode 302, which decreases with increased distance away on the spatial dimension from the applied positive charge at the electrode 302. Also shown in the diagram, a positive charge distribution (of positive ions of the electrolytic fluid) is at a maximum at the electrode 303, which decreases with increased distance away on the spatial dimension from the applied negative charge at the electrode 303. For example, the negative charge distribution can be formed by an accumulation of hydroxyl ($OH^-$) ions that forms an electrical double layer at the electrode 302, thereby creating a basic pH environment in the regions of the double layer proximate the electrode 302. Also for example, the positive charge distribution can be formed by an accumulation of hydronium ($H_3O^+$) ions, and in some examples magnesium ($Mg^{2+}$) ions, that forms an electrical double layer at the electrode 303, thereby creating an acidic pH environment in the regions of the double layer proximate the electrode 303. If, for example, the applied net charges were switched (e.g., a net negative charge applied on the electrode 302 and a net positive charge applied on the electrode 303), the charge distribution would be inverted from the example currently shown in FIG. 3A.

Figure 3B:
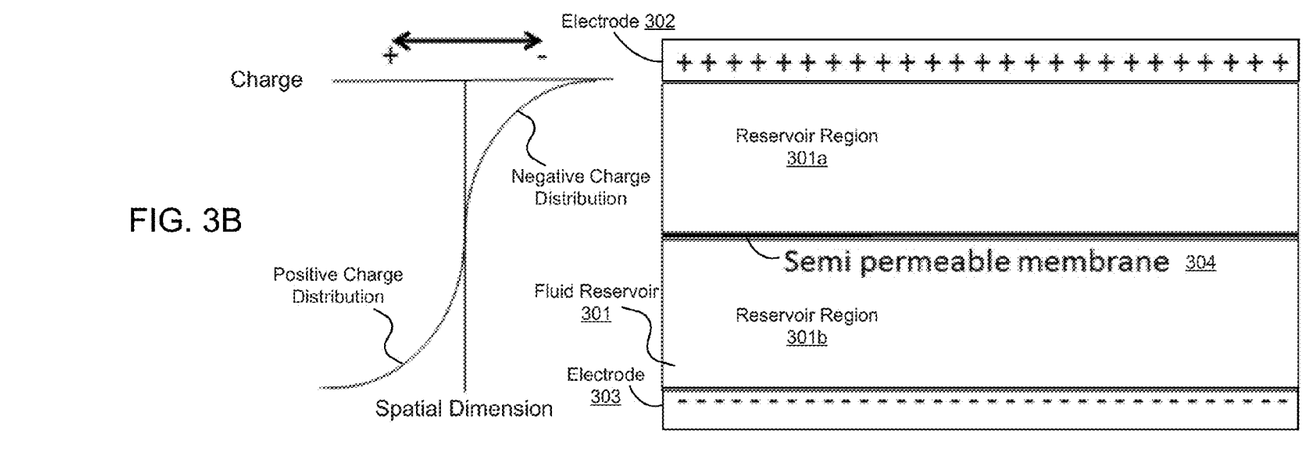

FIG. 3B shows another diagram depicting the charge distribution corresponding to a spatial dimension of the fluid reservoir 301 between the electrodes 302 and 303 in the exemplary non-thermal PCR device. In this example, the exemplary non-thermal PCR device includes a semi-permeable membrane 304 that separates a reservoir region 301a from a reservoir region 301b, in which the reservoir region 301a includes the electrode 302 and the reservoir region 301b includes the electrode 303. The semi-permeable membrane 304 is configured to be permeable to the ions in the electrolytic fluid and impermeable to the primers, polymerase enzymes, nucleotides, and nucleic acids. As shown in FIG. 3B, a net positive charge is applied along the electrode 302 and a net negative charge is applied along the electrode 303, thereby producing the respective negative ion and positive ion spatial distributions in the corresponding reservoir region 301a and 301b, respectively. In some implementations, for example, the exemplary PCR reagents (e.g., the primers, polymerase enzymes, nucleotides, and/or nucleic acids) can be added to only one side of the membrane, e.g., either reservoir region 301a or reservoir region 301b. This can provide additional control over the PCR process. For example, by adding the exemplary PCR reagents in the reservoir region 301b, the concentration of $Mg^{2+}$ ions can be manipulated to provide further control and influence over the denaturation, annealing, and/or elongation stages. Additionally for example, in some implementations, the semi-permeable membrane can be moved along the spatial dimension, e.g., which can provide further control on the positioning of the exemplary PCR reagents in the spatial ion distribution of each of the reservoir regions 301a and 301b of the fluid chamber 301.

Figure 3C:
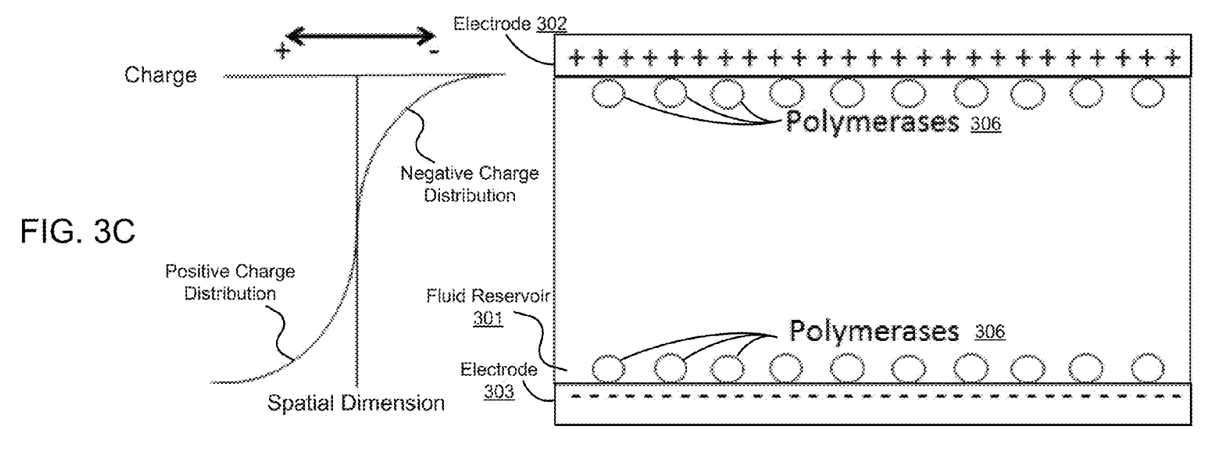

FIG. 3C shows a diagram depicting the charge distribution corresponding to a spatial dimension of the fluid reservoir 301 between the electrodes 302 and 303 in an exemplary non-thermal PCR device including polymerase enzymes 306 attached to the electrodes 302 and 303. For example, attached polymerase enzymes can improve operation in electrolytic solutions with high conductivity where the electrical double layer does not extend longer distances by limiting PCR close to surface. As shown in FIG. 3C, a net positive charge is applied along the electrode 302 and a net negative charge is applied along the electrode 303, thereby producing a greater negative charge distribution (of negative ions of the electrolytic fluid) proximate to the electrode 302 and decreasing with increased distance away from the applied positive charge at the electrode 302, and producing a greater positive charge distribution (of positive ions of the electrolytic fluid) proximate to the electrode 303 and decreasing with increased distance away from the applied negative charge at the electrode 303.

Figure 3D:
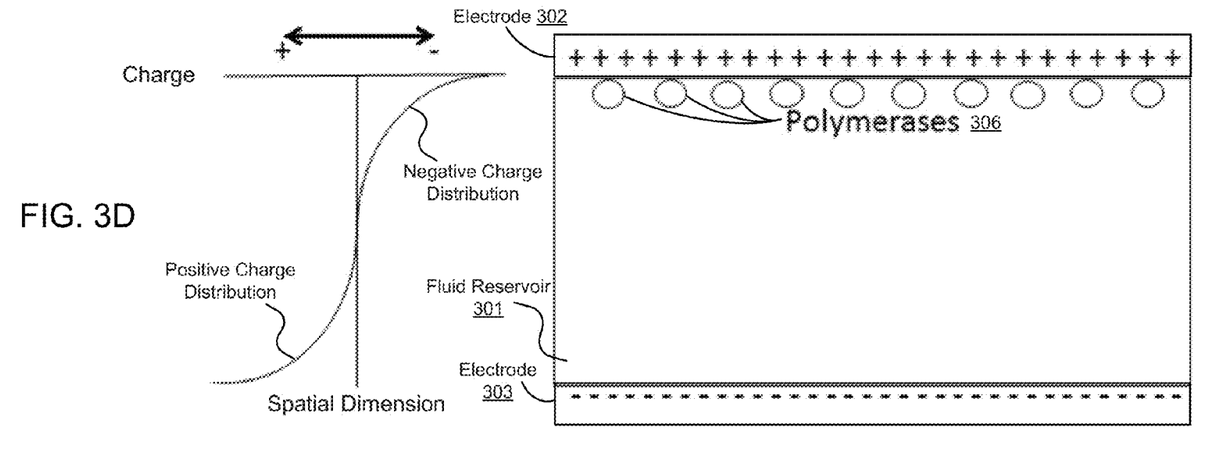
Figure 3E:
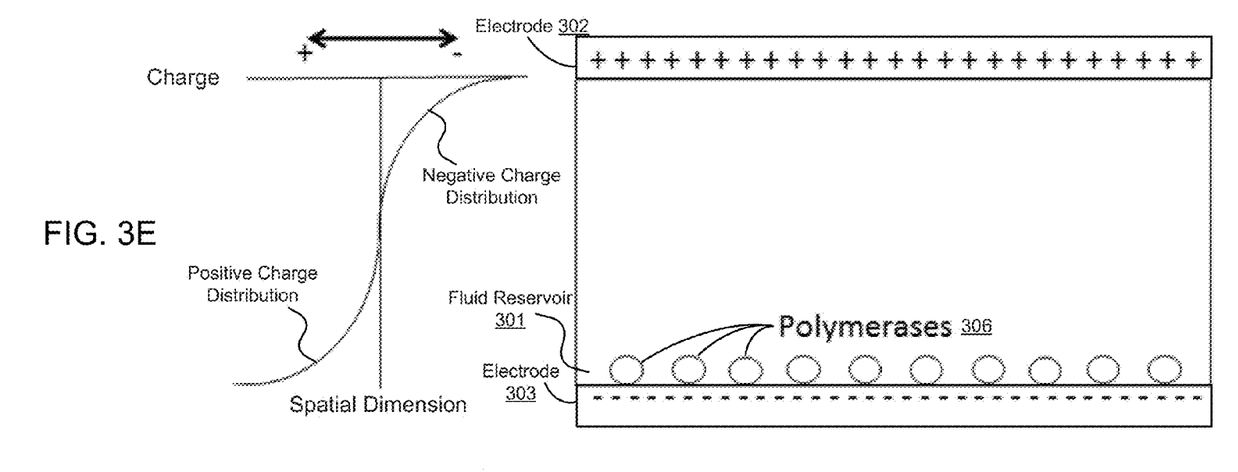

FIGS. 3D and 3E show diagrams of exemplary configurations of the exemplary non-thermal PCR device of FIG. 3C with the polymerase enzymes 306 attached to one of the two electrodes, e.g., the electrode 302 in FIG. 3D and the electrode 303 in FIG. 3E. In these configurations, further control of the PCR processes is provided by restricting the polymerase to only one side of the fluid chamber 301, e.g., which can trigger the bioactivity of annealing and/or elongation to only an acidic or only a basic pH environment, as desired.

Figure 3F:
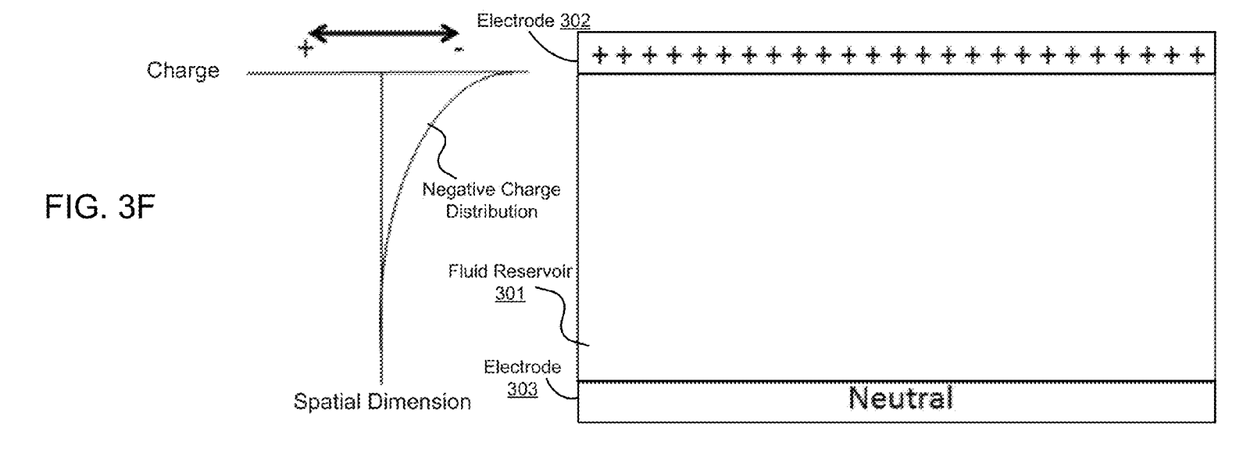

FIG. 3F shows a diagram depicting the charge distribution corresponding to a spatial dimension of the fluid reservoir 301 between the electrodes 302 and 303 in an exemplary non-thermal PCR device, in which one electrode (e.g., the electrode 303 in FIG. 3F) is configured to exhibit no net or neutral charge. In some implementations, for example, only one electrode can be configured in the fluid chamber 301. As shown in FIG. 3F, a net positive charge is applied along the electrode 302, thereby producing a negative charge distribution (of negative ions of the electrolytic fluid) proximate to the electrode 302 and decreasing with increased distance away from the applied positive charge at the electrode 302. In this example, no substantial positive charge distribution is produced based on the configurations and operating conditions of the exemplary device.

Figure 3G:
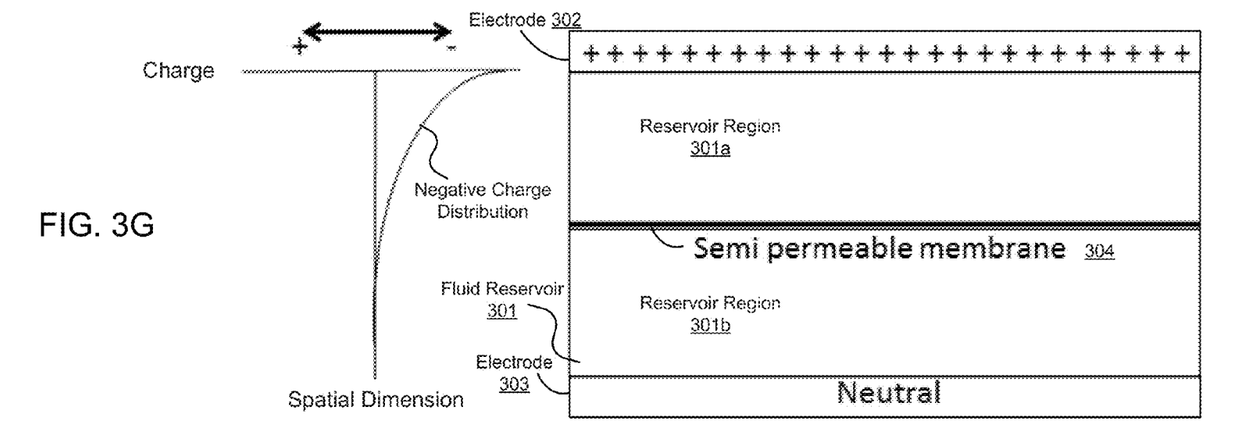

FIG. 3G shows a diagram of the exemplary configuration of the exemplary non-thermal PCR device of FIG. 3F, but also including the semi-permeable membrane 304 that separates the reservoir region 301a from the reservoir region 301b, in which the reservoir region 301a includes the positively charged electrode 302 and the reservoir region 301b includes the neutral electrode 303. For example, in this configuration, PCR reagents may be added to only one region (either the reservoir region 301a or 301b), and therefore the PCR reaction can be limited to only one side preferentially. This configuration can be advantageous if one needs to limit the reaction to the region with higher $Mg^{2+}$ concentration (e.g., reservoir region 301b) or with lower $Mg^{2+}$ concentration (e.g., reservoir region 301a). Also, for example, by adjusting the position of the semi-permeable membrane 304, the reaction can be limited to a particular sub-region, which may be beneficial for improving efficiency of the reaction. If, for example, the applied net charge was switched (e.g., to a net negative charge applied on the electrode 302), the charge distribution would be inverted from the example currently shown in FIG. 3G.

Figure 3H:
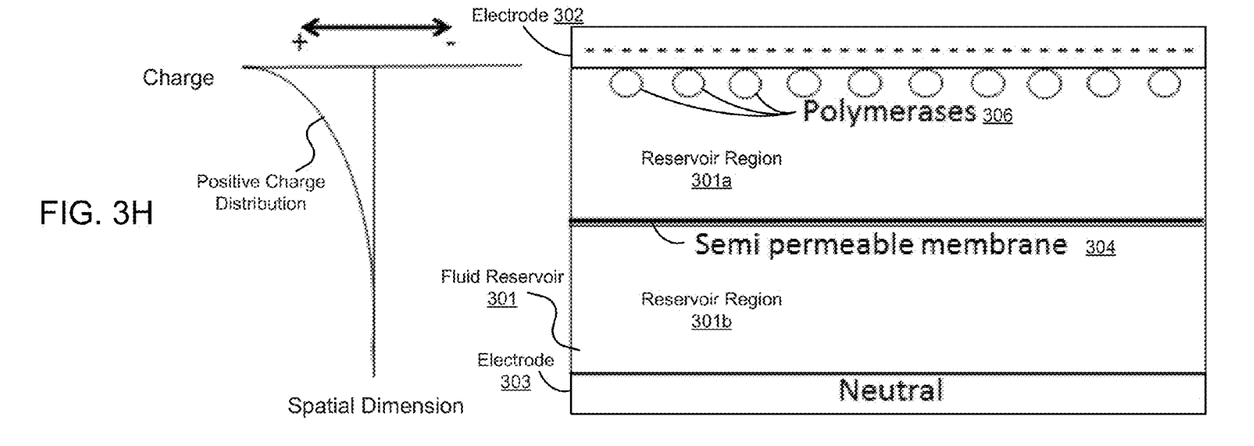

FIG. 3H also shows a diagram of the exemplary configuration of the exemplary non-thermal PCR device of FIG. 3F, but also with a net negative charge applied to the electrode 302 and including polymerase enzymes 306 attached to the electrode 302 and the semi-permeable membrane 304 that separates the reservoir region 301a from the reservoir region 301b, in which the reservoir region 301a includes the negatively charged electrode 302 and the reservoir region 301b includes the neutral electrode 303.

Figure 3I:
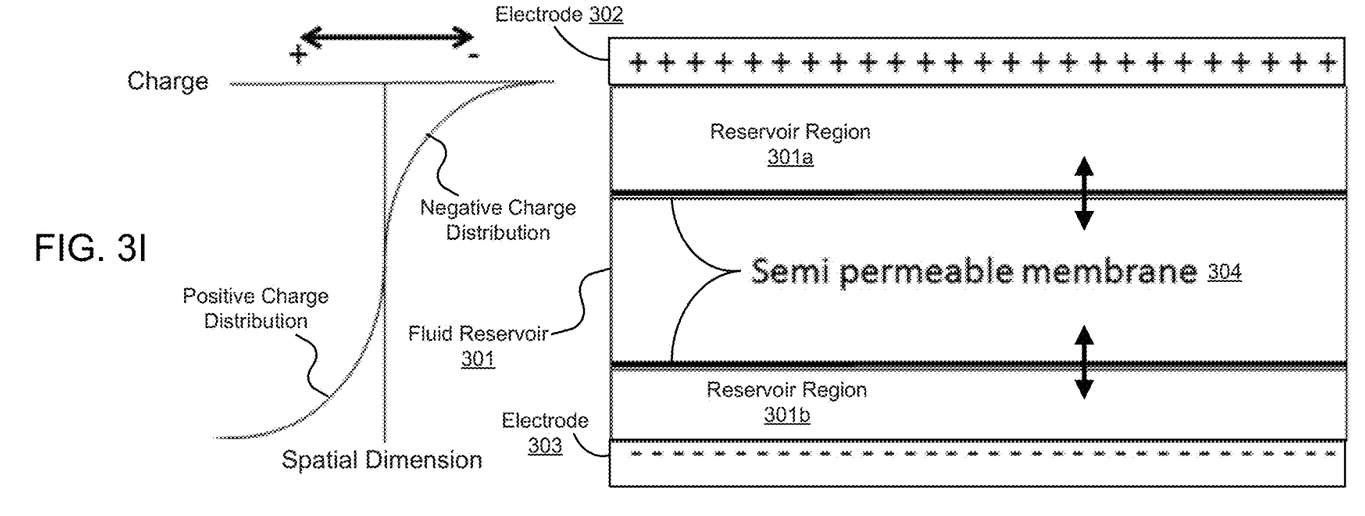

FIG. 3I shows a diagram depicting the charge distribution corresponding to a spatial dimension of the fluid reservoir 301 between the electrodes 302 and 303 of an exemplary non-thermal PCR device that includes multiple moveable semi-permeable membranes 304 that separate multiple regions of the fluid reservoir, e.g., shown in this example to include the reservoir region 301a including the electrode 302 and the reservoir region 301b including the electrode 303. The multiple moveable semi-permeable membranes 304 are configured to be permeable to the ions in the electrolytic fluid and impermeable to the primers, polymerase enzymes, nucleotides, and nucleic acids. As shown in FIG. 3I, a net positive charge is applied along the electrode 302 and a net negative charge is applied along the electrode 303, thereby producing the respective negative ion and positive ion spatial distributions in the corresponding reservoir region 301a and 301b, respectively. By adjusting the position of one or more of the semi-permeable membranes 304, for example, the PCR reactions can be limited to particular sub-regions within the reservoir region 301a and 301b, which can beneficially improve the efficiency of the reaction. In some implementations, for example, the exemplary PCR reagents can be added to only one side of the membrane, e.g., either the reservoir region 301a or the reservoir region 301b. In some implementations, for example, at least one or more of the multiple semi-permeable membranes 304 can be configured to be stationary (non-moveable).

The disclosed methods, systems, and devices can be used to provide a variety of advantages and benefits. For example, the disclosed PCR technology does not rely on the use of temperature for PCR cycling. Rather electric fields can be applied through electrodes that influence small ions (e.g., $H^+$, $OH^-$ and $Mg^{2+}$) to create local charge or pH distributions that can turn the activity of polymerase 'on' or 'off', and thus start or stop denaturation/hybridization reactions. For example, implementations of the disclosed PCR techniques can provide faster PCR cycling, e.g., since small ion migration due to electromagnetic fields is significantly faster than thermal equilibration in solution in molecular scale. For example, the disclosed PCR techniques can provide a direct and immediate effect on the operation of polymerase via control of magnesium ions ($Mg^{2+}$) in the electrolyte solution. Polymerase is a magnesium-dependent ion, and the concentration of magnesium in the vicinity of polymerase can be increased. Also for example, by controlling the makeup of the electrolytic solution and the magnitude of the electric field, the localized regions at a controllable pH be created, e.g., via spatial distributions of the ions in the fluid volume, which can control DNA denaturation and hybridization, e.g. by effectively 'turning on' or 'turning off' the polymerase activity. In some examples, the disclosed technology can provide portable, battery-based solutions for PCR. For thermal generation, media with high resistance is used on almost every thermal system, which uses significantly higher power compared to the working conditions of the disclosed methods, systems, and devices, where relatively higher impedance solutions can be used that require very little current and voltage. In some examples, the disclosed technology can provide smooth integration with electrophoresis and dielectrophoresis technologies without additional fabrication processes, e.g., thus allowing low cost integrated solutions including sample handling, purification and preparation steps. For example, the applied electric fields can be used to concentrate molecules by electrophoretic techniques and increase the probability of certain interactions as a mechanism for amplification. In one example of an electrophoretic technique, the large molecules of the PCR reactions, e.g., oligonucleotides, can be made to move and accumulate at specific locations in the fluid chamber.

Figure 4A:
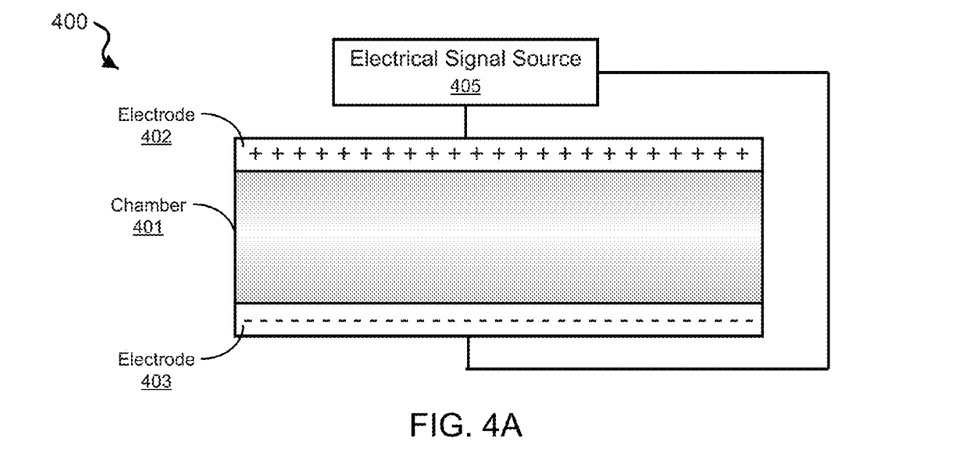
FIGS. 4A-4C show schematic illustrations of exemplary fluidic PCR chip devices.

In some aspects, the disclosed technology can be implemented on a fluidic chip device and can be compatible with standard sample preparation and detection platforms for PCR. In one embodiment, a fluidic PCR chip device 400 can contain a reservoir or fluid chamber 401 covered with two metal electrodes 402 and 403 positioned at opposite sides of the chamber. An exemplary schematic of the fluidic PCR chip device 400 is shown in FIG. 4A. Different heights (e.g., distance between the electrodes) and geometries of the electrodes 402 and 403 can be used for maximum efficiency and engineering of the diffuse layer and electric double layer. The fluidic PCR chip device 400 can be electrically interfaced with an electrical signal source 405 (e.g., function generator), which can be included in such standard PCR platforms, to provide the applied voltage at the electrodes 402 and 403.

The PCR chip device 400 can be operated to implement the stages of charge cycling for PCR. For example, for denaturation, low pH and/or high pH can be generated, e.g., based on the electrode configurations and/or applied electrical signal on the electrodes. For example, for annealing and denaturation, different pH levels can be generated. Different chamber heights can be configured in the fluid chamber 401 to affect the PCR cycling. For example, the device 450 can include an inlet and outlet port or region. Other exemplary configurations can include the following, for example. Polymerase enzymes can be attached to a surface while primers and template DNAs are free in solution. Primer oligonucleotides can be attached to a surface while polymerase and template DNAs are free in solution. Reaction solution can be kept stationary while the applied voltages to the electrodes are altered.

Figure 4B:
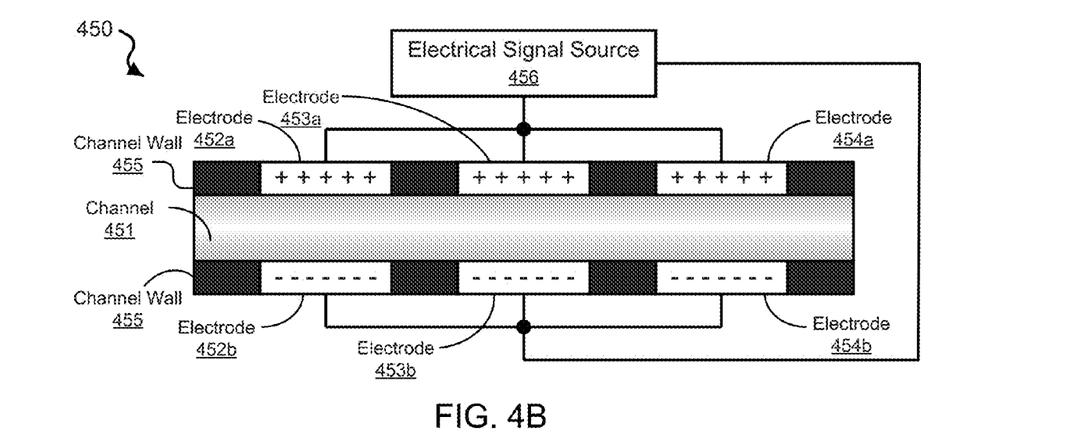

In another exemplary embodiment, a fluidic PCR chip device 450 for cycling PCR includes a substrate 455 that is electrically insulating having a channel 451, or a plurality of channels 451, structured to carry the electrolytic fluid, e.g., including continuous or intermittent flow rates. The fluidic PCR chip device 450 includes two or more electrode pairs, e.g., such as electrode pairs 452, 453, and 454, in which each electrode pair is located in the channel 451 in contact with the electrolytic surface and spaced apart along the channel. An exemplary schematic of the fluidic PCR chip device 400 is shown in FIG. 4B. The fluidic PCR chip device 450 can be electrically interfaced to an electrical signal source 456 that is electrically coupled to the electrode pairs 452, 453, and 454 to apply electric fields of varying magnitude or other electric field parameters to generate varying pH levels of the electrolytic fluid in regions proximate the electrode pairs 452, 453, and 454. For example, the electrical signal source 456 can apply a first electric field across the electrode pair 452 to generate a first pH level of the electrolytic fluid, in which the double-stranded nucleic acid is capable of denaturation to at least partial single strands at the first pH level. For example, the electrical signal source 456 can apply a second electric field across the electrode pair 453 to generate a second pH level of the electrolytic fluid, in which the second pH level enables one or both of binding of a polymerase enzyme and a primer with a corresponding segment of the at least partial single strands and synthesis of new complementary nucleic acid strands from the nucleotides using the at least partial single strands. For example, the electrical signal source 456 can apply a third electric field across the electrode pair 454 to generate a third pH level of the electrolytic fluid for synthesis of new complementary nucleic acid strands from the nucleotides using the at least partial single strands.

The fluidic PCR chip device 450 can be operated to implement the stages of charge cycling for PCR. For example, for denaturation, low pH and/or high pH can be generated, e.g., based on the electrode configurations and/or applied electrical signal on the electrodes. For example, for annealing and denaturation, different pH levels can be generated. Different channel heights, lengths, and spacings between electrode pairs can be configured in the fluidic channel 451 to affect the PCR cycling. For example, the device 450 can include an inlet and outlet port or region. Other exemplary configurations can include the following, for example. Polymerase enzymes can be attached to an interior surface of the channel 451 while primers and template DNAs are free in solution. Primer oligonucleotides can be attached to a surface while polymerase and template DNAs are free in solution. The reaction solution can be kept stationary in the channel 451 while the applied voltages to the electrodes are applied, and in some examples, altered. In other examples, the reaction solution can be encapsulated in a droplet like cavity and continuously flowed through channel path into alternating electric field regions in which the charge distribution within the cavity can be altered.

Figure 4C:
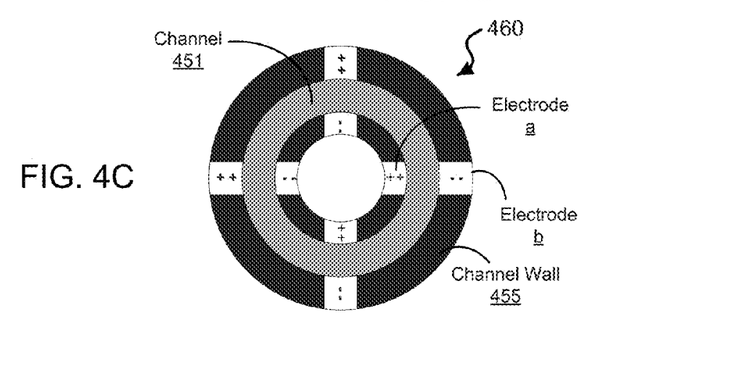

In some implementations, for example, the channel 451 can be wrapped around in a spiral or repeating curved or linear patterns, among others, to provide multiple two or more electrode pair segments of the channel 451 corresponding to a number of desired repeated PCR cycles. FIG. 4C shows a schematic diagram of a fluidic PCR chip device 460 that includes a circular geometry having a plurality of electrode pairs (of outer electrodes b and inner electrodes a) configured on the substrate 455 spaced along positions on the interior of the channel 451. For example, the device 460 can include an inlet and outlet port or region to receive and remove the electrolytic fluid.

Figure 5:
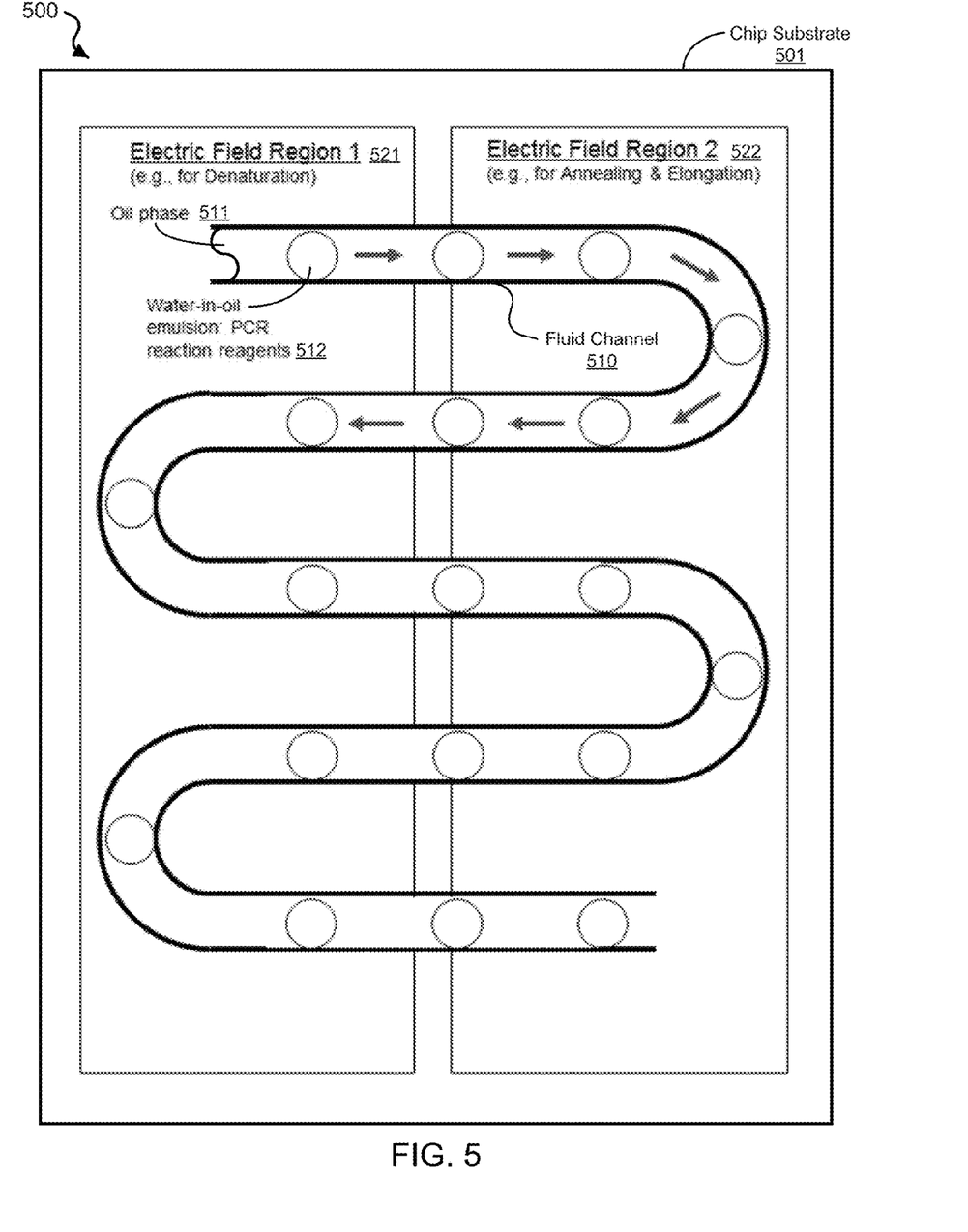
FIG. 5 shows a schematic illustration of an exemplary PCR microfluidic chip device.

FIG. 5 shows a schematic diagram of a PCR microfluidic chip device 500. The PCR microfluidic chip device 500 includes a chip substrate 501, which can be of a material that is electrically insulative. The PCR microfluidic chip device 500 includes a fluidic channel 510 structured to carry an electrolytic fluid, e.g., including ions and PCR reagents, including but not limited to primers, polymerase enzymes, nucleotides, and nucleic acids. In some implementations, for example, the electrolytic fluid can include water-in-oil emulsion droplets 512 in an oil phase fluid 511 that flow through the fluidic channel 510. In some implementations, for example, the fluidic channel 510 can be configured on the substrate 501 as an enclosed channel formed of an electrically insulative material. In the exemplary configuration shown in FIG. 5, for example, the fluidic channel 510 is structured in a geometry to wrap in a repeating linear and curved pattern. The fluidic channel 510 is configured to run through two or more regions configured to apply differing electric fields, e.g., of different electric field magnitudes and/or other electric field parameters, which are shown in the exemplary embodiment in FIG. 5 as an electric field region 521 and an electric field region 522 of the PCR microfluidic chip device 500. The different electric fields applied across the portions of the fluidic channel 510 that pass through the respective electric field regions 521 and 522 can be applied using two or more corresponding electrode pairs. In some implementations, for example, each electrode pair can be located along the channel 510 in contact with the electrolytic surface. In some implementations, for example, the PCR microfluidic chip device 500 can include an inlet and outlet port or region to receive and remove the electrolytic fluid. In some implementations, for example, the PCR microfluidic chip device 500 can include electrical interface components electrically coupled to the corresponding electrode pairs via electrically conductive conduits, e.g., in which the conduits can be enclosed within the electrically insulative material of the substrate 501. For example, the electrode pairs are capable of receiving applied electrical signals from an external electrical circuit electrically coupled to the electrical interface components, in which the applied electrical signals can produce a first electric field across an electrode pair in the electric field region 521 to generate a first pH level of the electrolytic fluid, e.g., such that double-stranded nucleic acid is capable of denaturation at the first pH level (e.g., to form single-stranded nucleic acid molecules or at least partial single strand regions of the double-stranded nucleic acid), as well as the applied electrical signals can produce a second electric field across an electrode pair in the electric field region 522 to generate a second pH level of the electrolytic fluid, e.g., which can enable the binding of polymerase and a primer with a corresponding segment of the single nucleic acid strands (e.g., annealing) and/or the synthesis of new complementary nucleic acid strands from the available nucleotides and the single strands (e.g., elongation). For example, the exemplary water-in-oil emulsion droplets 512 in the oil phase 511 of the electrolytic fluid that flows through the fluidic channel 510 passes through the electric field region 521 and the electric field region 522 and undergoes different applied electric fields, e.g., resulting in alternating charge distributions within droplets.

These exemplary embodiments can be implemented in a handheld package slightly larger than a smartphone. For example, such portable configurations of the disclosed devices can enable the implementation of quantitative real-time PCR (qPCR), which can replace slow, labor-intensive methods of qPCR with rapid, low-cost testing. Such a device would be benefit public health as discussed briefly below.

Widespread testing to identify diseases or genetic defects is a worldwide problem due to cost and availability, especially in the developing world, but also in the developed world. For example, hospital associated infections (HAI) lead to nearly 100,000 deaths every year only in the United States according to the Centers for Disease Control and Prevention (CDC). These infections acquired during the hospital stay contribute to significant patient morbidity and increase the likelihood of death by 35% in critically ill patients and result in limited antimicrobial treatment options. Once a patient has been suspected to be a potential carrier for an HAI like MRSA, for example, most hospitals use slow bacterial culture tests taking at least 48 hours to produce results and put patients pending results on preemptive isolation.

As an alternative to slow bacteria culture tests, quantitative PCR (qPCR) testing has been recommended by the CDC and others. Techniques using qPCR seemly could substantially improve detection techniques of HAI as qPCR can provide higher sensitivity and efficacy with faster results than bacteria culture tests, e.g., in as soon as two hours, making preemptive isolation unnecessary, and thus may reduce the risk of transmission because patients with positive results can be identified and placed on isolation sooner. However, based on the current cost of qPCR technologies, it may cost more than $10 billion in total to hospitals to test every single patient admitted to hospitals (universal screening). Also, if the duration of each test and allocation of personnel are added into the equation, universal screening cannot be considered as a practical solution. Additionally, qPCR bench-top devices require sensitive sample preparation, high per test costs, and are susceptible to contamination. Moreover, other technologies show no potential to be integrated in a hand-held package and suitable for various settings. All PCR and qPCR technologies on the market use thermal cycling to achieve PCR.

The disclosed technology can automate qPCR in an ultraportable package allowing qPCR tests to be performed at the point of care, as shown in FIG. 4. In one example, non-thermal cycling qPCR can be implemented in a single-use, microfluidic chip system that fully integrates and automates the sample preparation, amplification, and detection processes required for qPCR, thereby eliminating the need for skilled personnel and preventing contamination, as well as be small enough to fit in the palm of your hand and be operated for extended periods on battery power. For example, PCR cycling for complete amplification and detection of DNA can occur in less than 15 minutes, e.g., which is significantly shorter than conventional qPCR.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A device for cycling polymerase chain reaction (PCR), comprising:
    a container including an interior surface formed of an electrically insulative material and structured to contain an electrolytic fluid including ions, primers, polymerase enzymes, nucleotides, and a double-stranded nucleic acid;
    a first electrode and a second electrode configured on an interior surface of the container in contact with the electrolytic fluid; and
    a circuit electrically coupled to the first and second electrodes to apply a first electric field across the first and second electrode to generate a first pH level of the electrolytic fluid, wherein the double-stranded nucleic acid is capable of denaturation to at least partial single strands at the first pH level, and to apply a second electric field across the first and second electrodes to generate a second pH level of the electrolytic fluid, wherein the second pH level enables at least one of binding of a polymerase enzyme and a primer with a corresponding segment of the at least partial single strands or synthesis of new complementary nucleic acid strands from the nucleotides using the at least partial single strands.

2. The device as in claim 1, further comprising a semi-permeable membrane configured within the interior of the container and structured to separate an interior of the container into a first region including the first electrode and a second region including the second electrode, the semi-permeable membrane permeable for the ions to traverse the membrane and impermeable to the primers, polymerase enzymes, nucleotides, and double-stranded nucleic acid.

3. The device as in claim 2, wherein the semi-permeable membrane is moveable within the container to adjust a volume of the first or the second region.

4. The device as in claim 1, wherein the polymerase enzymes are covalently attached to a surface of the fluid chamber.

* * * * *